US005510309A

United States Patent [19]

Chang et al.

[11] Patent Number: 5,510,309
[45] Date of Patent: Apr. 23, 1996

[54] METHOD FOR PREPARING A MODIFIED SOLID OXIDE

[75] Inventors: Clarence D. Chang, Princeton, N.J.;
Charles T. Kresge, West Chester, Pa.;
Jose G. Santiesteban, Yardley, Pa.;
James C. Vartuli, West Chester, Pa.

[73] Assignee: Mobil Oil Corporation, Fairfax, Va.

[21] Appl. No.: 236,073

[22] Filed: May 2, 1994

[51] Int. Cl.$^6$ ........................................ B01J 23/30
[52] U.S. Cl. .................. 502/308; 502/309; 502/321; 502/349; 502/350; 208/46
[58] Field of Search ........................ 502/308, 309, 502/349, 350, 321; 208/46

[56] References Cited

U.S. PATENT DOCUMENTS

| | | | |
|---|---|---|---|
| 3,450,777 | 6/1969 | Mizutani et al. | 260/641 |
| 4,049,575 | 9/1977 | Sasaki et al. | 502/213 |
| 4,263,457 | 4/1981 | Takeda et al. | 585/430 |
| 5,004,846 | 4/1991 | Sato et al. | 502/77 |
| 5,113,034 | 5/1992 | Soled et al. | 585/510 |

FOREIGN PATENT DOCUMENTS 1-288339  11/1989  Japan.

OTHER PUBLICATIONS

European Publication No. WO 94/14732 (Jul. 7, 1994).

Hino, M. et al., "Synthesis of Solid Superacid of Tungsten Oxide supported on Zirconia and its Catalytic Action for Reactions of Butane and Pentane," J. Chem. Soc. Chem. Comm., 1259–1260 (1988).

Arata, K. et al., "Synthesis of Solid Superacid of Tungsten Oxide Supported on Zirconia and its Catalytic Action," Proceedings 9th International Congress on Catalysis, 4, 1727–1735 (1988).

Primary Examiner—Anthony McFarlane
Attorney, Agent, or Firm—Malcolm D. Keen; Dennis P. Santini; Lori F. Cuomo

[57] ABSTRACT

There is provided a method for preparing an acidic solid comprising a Group IVB metal oxide modified with an oxyanion of a Group VIB metal. An example of this acidic solid is zirconia, modified with tungstate. This modified solid oxide may be used as a catalyst, for example, to isomerize $C_4$ to $C_8$ paraffins. The modified solid oxide is prepared by co-precipitating the Group IVB metal oxide along with the oxyanion of the Group VIB metal.

17 Claims, No Drawings

METHOD FOR PREPARING A MODIFIED SOLID OXIDE

BACKGROUND

There is provided a method for preparing an acidic solid comprising a Group IVB metal oxide modified with an oxyanion of a Group VIB metal. This modified solid oxide may be used as a catalyst, for example, to isomerize $C_4$ to $C_8$ paraffins. The modified solid oxide is prepared by co-precipitating the Group IVB metal oxide along with the oxyanion of the Group VIB metal.

The present catalysts, especially tungstate-modified zirconia catalysts, are useful for many hydrocarbon conversion processes such as paraffin isomerization, ring opening of cyclics, alkylation of naphthalene, hydrocracking, etc. These catalysts may be prepared by a complex impregnation procedure involving numerous steps including the precipitation of zirconia precursor, refluxing, two filtration/washing/reslurry steps, impregnation with tungsten, and a final calcination. In accordance with the present method, this complex procedure is reduced to just three steps: co-precipitation of tungsten with the zirconia precursor, filtration, and calcination.

The present method produces a better catalyst at lower manufacturing cost (fewer steps) and is more flexible to address the environmental concerns (eliminates the requirement for a chloride salt).

The solid material described herein comprises an oxide of a Group IVB metal, preferably zirconia or titania. This Group IVB metal oxide is modified with an oxyanion of a Group VIB metal, such as an oxyanion of tungsten, such as tungstate. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; in Japanese Kokai Patent Application No. Hei 1 [1989]-288339; and in an article by K. Arata and M. Hino in *Proceedings 9th International congress on Catalysis*, volume 4, pages 1727–1735 (1988), the entire disclosures of these publications are expressly incorporated herein by reference. According to these publications, tungstate is impregnated onto a preformed solid zirconia material.

For the purposes of the present disclosure, the expression, Group IVB metal oxide modified with an oxyanion of a Group VIB metal, is intended to connote a material comprising, by elemental analysis, a Group IVB metal, a Group VIB metal and oxygen, with more acidity than a simple mixture of separately formed Group IVB metal oxide mixed with a separately formed Group VIB metal oxide or oxyanion. The present Group IVB metal, e.g., zirconium, oxide modified with an oxyanion of a Group VIB metal, e.g., tungsten, is believed to result from an actual chemical interaction between a source of a Group IVB metal oxide and a source of a Group VIB metal oxide or oxyanion.

This chemical interaction is discussed in the aforementioned article by K. Arata and M. Hino in *Proceedings 9th International Congress on catalysis*, volume 4, pages 1727–1735 (1988). In this article, it is suggested that solid superacids are formed when sulfates are reacted with hydroxides or oxides of certain metals, e.g., Zr. These superacids are said to have the structure of a bidentate sulfate ion coordinated to the metal, e.g., Zr. In this article, it is further suggested that a superacid can also be formed when tungstates are reacted with hydroxides or oxides of Zr. The resulting tungstate modified zirconia materials are theorized to have an analogous structure to the aforementioned superacids comprising sulfate and zirconium, wherein tungsten atoms replace sulfur atoms in the bidentate structure.

Although it is believed that the present catalysts may comprise the bidentate structure suggested in the aforementioned article by Arata and Hino, the particular structure of the catalytically active site in the present Group IVB metal oxide modified with an oxyanion of a Group VIB metal has not yet been confirmed, and it is not intended that this catalyst component should be limited to any particular structure.

SUMMARY

There is provided a method for preparing an acidic solid comprising a Group IVB metal oxide modified with an oxyanion of a Group VIB metal, said method comprising co-precipitating a Group IVB metal oxide along with an oxyanion of a Group VIB metal.

There is also provided a method for preparing an acidic solid comprising tungstate-modified zirconia, said method comprising the steps of:

(a) combining a first liquid solution with a second liquid solution, said first solution comprising a source of zirconia dissolved in water and said second solution comprising a source of tungstate dissolved in water;

(b) maintaining the combined solutions of step (a) under conditions sufficient to form a solid co-precipitate comprising tungstate-modified zirconia;

(c) recovering the solid co-precipitate from step (b) by filtration; and (d) calcining the recovered co-precipitate from step (c).

EMBODIMENTS

Suitable sources of the Group IVB metal oxide, used for preparing the present catalyst, include compounds capable of generating such oxides, such as oxychlorides, chlorides, nitrates, oxynitrates, etc., particularly of zirconium or titanium. Alkoxides of such metals may also be used as precursors or sources of the Group IVB metal oxide. Examples of such alkoxides include zirconium n-propoxide and titanium i-propoxide. These sources of a Group IVB metal oxide, particularly zirconia, may form zirconium hydroxide, i.e., $Zr(OH)_4$, or hydrated zirconia as intermediate species upon precipitation from an aqueous medium in the absence of a reactive source of tungstate. The expression, hydrated zirconia, is intended to connote materials comprising zirconium atoms covalently linked to other zirconium atoms via bridging oxygen atoms, i.e., Zr—O—Zr, further comprising available surface hydroxy groups. When hydrated zirconia is impregnated with a suitable source of tungstate under sufficient conditions, these available surface hydroxyl groups are believed to react with the source of tungstate to form an acidic catalyst. As suggested in the aforementioned article by K. Arata and M. Hino in *Proceedings 9th International Congress on Catalysis*, volume 4, pages 1727–1735 (1988), precalcination of $Zr(OH)_4$ at a temperature of from about 100° C. to about 400° C. results in a species which interacts more favorably with tungstate upon impregnation therewith. This precalcination is believed to result in the condensation of ZrOH groups to form a polymeric zirconia species with surface hydroxyl groups. This polymeric species is referred to herein as a form of a hydrated zirconia.

Suitable sources for the oxyanion of the Group VIB metal, preferably molybdenum or tungsten, include, but are not limited to, ammonium metatungstate or metamolybdate, tungsten or molybdenum chloride, tungsten or molybdenum carbonyl, tungstic or molybdic acid and sodium tungstate or molybdate.

The present modified oxide material may be prepared by combining a first liquid solution comprising a source of a Group IVB metal oxide with a second liquid solution comprising a source of an oxyanion of a Group VIB metal. This combination of two solutions takes place under conditions sufficient to cause co-precipitation of the modified oxide material as a solid from the liquid medium. Alternatively, the source of the Group IVB metal oxide and the source of the oxyanion of the Group VIB metal may be combined in a single liquid solution. This solution may then be subjected to conditions sufficient to cause co-precipitation of the solid modified oxide material, such as by the addition of a precipitating reagent to the solution. Water is a preferred solvent for these solutions.

The temperature at which the liquid medium is maintained during the co-precipitation may be less than about 200° C., e.g., from about 0° C. to about 200° C. This liquid medium may be maintained at an ambient temperature (i.e., room temperature) or the liquid may be cooled or heated. A particular range of such temperatures is from about 50° C. to about 100° C.

The liquid medium from which the present catalyst components are co-precipitated may optionally comprise a solid support material, in which case the present catalyst may be coprecipitated directly onto the solid support material. Examples of such support materials include the material designated M41S, which is described in U.S. Pat. No. 5,102,643. A particular example of such an M41S material is a material designated MCM-41, which is described in U.S. Pat. No. 5,098,684.

Support materials and/or co-catalyst materials may also, optionally, be co-precipitated from the liquid medium along with the Group IVB metal oxide and the oxyanion of the Group VIB metal. An example of a co-catalyst material is a hydrogenation/dehydrogenation component.

According to an optional modification of the solid material described herein, a hydrogenation/dehydrogenation component is combined with the material. This hydrogenation/dehydrogenation component imparts the ability of the material to catalyze the addition of hydrogen to or the removal of hydrogen from organic compounds, such as hydrocarbons, optionally substituted with one or more heteroatoms, such as oxygen, nitrogen, metals or sulfur, when the organic compounds are contacted with the modified material under sufficient hydrogenation or dehydrogenation conditions.

Examples of hydrogenation/dehydrogenation components include the oxide, hydroxide or free metal (i.e., zero valent) forms of Group VIII metals (i.e., Pt, Pd, Ir, Rh, Os, Ru, Ni, Co and Fe), Group IVA metals (i.e., Sn and Pb), Group VB metals (i.e., Sb and Bi) and Group VIIB metals (i.e., Mn, Tc and Re). The present catalyst may comprise one or more catalytic forms of one or more noble metals (i.e., Pt, Pd, Ir, Rh, Os or Ru). Combinations of catalytic forms of such noble or non-noble metals, such as combinations of Pt with Sn, may be used. The valence state of the metal of the hydrogenation/dehydrogenation component is preferably in a reduced valance state, e.g., when this component is in the form of an oxide or hydroxide. The reduced valence state of this metal may be attained, in situ, during the course of a reaction, when a reducing agent, such as hydrogen, is included in the feed to the reaction.

Other elements, such as alkali (Group IA) or alkaline earth (Group IIA) compounds may optionally be added to or co-precipitated with the present catalyst to alter catalytic properties. The addition of such alkali or alkaline earth compounds to the present catalyst may enhance the catalytic properties of components thereof, e.g., Pt or W, in terms of their ability to function as a hydrogenation/dehydrogenation component or an acid component.

The Group IVB metal (i.e., Ti, Zr or Hf) and the Group VIB metal (i.e., Cr, Mo or W) species of the present catalyst are not limited to any particular valence state for these species. These species may be present in this catalyst in any possible positive oxidation value for these species. Subjecting the catalyst, e.g., when the catalyst comprises tungsten, to reducing conditions, e.g., believed to be sufficient to reduce the valence state of the tungsten, may enhance the overall catalytic ability of the catalyst to catalyze certain reactions, e.g., the isomerization of n-hexane.

The modified acidic oxide may be contacted with hydrogen at elevated temperatures. These elevated temperatures may be 100° C. or greater, e.g., 250° C. or greater, e.g., about 300° C. The duration of this contact may be as short as one hour or even 0.1 hour. However, extended contact may also be used. This extended contact may take place for a period of 6 hours or greater, e.g., about 18 hours. When zirconia is modified with tungstate and then contacted with hydrogen at elevated temperatures, an increase in catalytic activity, e.g., for paraffin isomerization, has been observed. The modified acidic oxide may be contacted with hydrogen in the presence or absence of a hydrocarbon cofeed. For example, the activity of the catalyst may be increased, in situ, during the course of a reaction, such as hydrocracking, when a hydrocarbon and hydrogen are passed over the catalyst at elevated temperatures.

The optional hydrogenation/dehydrogenation component of the present catalyst may be derived from Group VIII metals, such as platinum, iridium, osmium, palladium, rhodium, ruthenium, nickel, cobalt, iron and mixtures of two or more thereof. Optional components of the present catalyst, which may be used alone or mixed with the above-mentioned hydrogenation/dehydrogenation components, may be derived from Group IVA metals, preferably Sn, and/or components derived from Group VIIB metals, preferably rhenium and manganese. These components may be added to the catalyst by methods known in the art, such as ion exchange, impregnation or physical admixture. For example, salt solutions of these metals may be contacted with the remaining catalyst components under conditions sufficient to combine the respective components. The metal containing salt is preferably water soluble. Examples of such salts include chloroplatinic acid, tetraammineplatinum complexes, platinum chloride, tin sulfate and tin chloride. The optional components may also be co-precipitated along with the other components of the modified oxide material.

When the present tungstate-modified zirconia catalyst is impregnated with platinum to form a catalyst particularly adapted to catalyze paraffin isomerization reactions, it has been discovered that it is desirable to co-precipitate about one percent by weight of Fe or Mn along with the solid precipitated from the aqueous mixture comprising the source of zirconia and the source of tungstate. Suitable iron salts, which may be included in this aqueous mixture, include $Fe(NO_3)_3$ and $Fe_2(SO_4)_3$.

The present modified oxide material may be recovered by filtration from the liquid medium, followed by drying.

Calcination of the resulting material may be carried out, preferably in an oxidizing atmosphere, at temperatures from about 500° C. to about 900° C., preferably from about 700° C. to about 850° C., and more preferably from about 750° C. to about 825° C. The calcination time may be up to 48 hours, preferably for about 0.1–24 hours, and more preferably for about 1.0–10 hours. In a most preferred embodiment, calcination is carried out at about 800° C. for about 1 to about 3 hours. The optional components of the catalyst (e.g., Group VIII metal, Group VIIB metal, etc.) may be added after or before the calcination step by techniques known in the art, such as impregnation, co-impregnation, co-precipitation, physical admixture, etc. The optional components, e.g., the hydrogenation/dehydrogenation component, may also be combined with the remaining catalyst components before or after these remaining components are combined with a binder or matrix material as described hereinafter.

In the present catalyst, of the Group IVB oxides, zirconium oxide is preferred; of the Group VIB anions, tungstate is preferred; and of the optional hydrogenation/dehydrogenation components, platinum and/or platinum-tin are preferred.

Qualitatively speaking, elemental analysis of the present acidic solid will reveal the presence of Group IVB metal, Group VIB metal and oxygen. The amount of oxygen measured in such an analysis will depend on a number of factors, such as the valence state of the Group IVB and Group VIB metals, the form of the optional hydrogenation/dehydrogenation component, moisture content, etc. Accordingly, in characterizing the composition of the present catalyst, it is best not to be restricted by any particular quantities of oxygen. In functional terms, the amount of Group VIB oxyanion in the present catalyst may be expressed as that amount which increases the acidity of the Group IVB oxide. This amount is referred to herein as an acidity increasing amount. Elemental analysis of the present catalyst may be used to determine the relative amounts of Group IVB metal and Group VIB metal in the catalyst. From these amounts, mole ratios in the form of $XO_2/YO_3$ may be calculated, where X is said Group IVB metal, assumed to be in the form $XO_2$, and Y is said Group VIB metal, assumed to be in the form of $YO_3$. It will be appreciated, however, that these forms of oxides, i.e., $XO_2$ and $YO_3$, may not actually exist, and are referred to herein simply for the purposes of calculating relative quantities of X and Y in the present catalyst. The present catalysts may have calculated mole ratios, expressed in the form of $XO_2/YO_3$, where X is at least one Group IVB metal (i.e., Ti, Zr, and Hf) and Y is at least one Group VIB metal (i.e., Cr, Mo, or W), of up to 1000, e.g., up to 300, e.g., from 2 to 100, e.g., from 4 to 30.

The amount of optional hydrogenation/dehydrogenation component may be that amount which imparts or increases the catalytic ability of the overall material to catalytically hydrogenate or dehydrogenate a hydrogenatable or dehydrogenatable organic compound under sufficient hydrogenation or dehydrogenation conditions. This amount is referred to herein as a catalytic amount. Quantitatively speaking, the present catalyst may comprise, for example, from about 0.001 to about 5 wt %, e.g., from about 0.1 to about 2 wt %, of the optional hydrogenation/dehydrogenation component, especially when this component is a noble metal.

Especially when the present catalyst includes a platinum hydrogenation/dehydrogenation component, this catalyst may also comprise up to about five weight percent of Fe and/or Mn, as measured by elemental analysis of the catalyst.

The present catalyst is acidic and may be observed as being highly acidic, even to the extent of being a superacid. For example, this catalyst, whether analyzed in the presence or absence of optional components (e.g., hydrogenation/dehydrogenation components) and/or binder materials, may have an acid strength of a superacid as measured by the color change of an appropriate indicator, such as the Hammett indicator. More particularly, the Ho acid strength of the present catalyst may have a value of less than −13, i.e., an "acid strength" of greater than −13. The use of Hammett indicators to measure the acidity of solid superacids is discussed in the Soled et al. U.S. Pat. No. 5,157,199. This Soled et al. patent also describes the Ho acid strength for certain sulfated transition metal superacids.

The catalyst described herein may be used as a catalyst for isomerizing $C_4$ to $C_8$ paraffins. Suitable feeds contain substantial amounts of normal and/or singly branched low octane $C_4$ to $C_8$ hydrocarbons. The feed may also contain appreciable amounts of $C_6$ and $C_7$ cyclic paraffins which may undergo ring-opening reactions.

The present isomerization process may be carried out by contacting the hydrocarbon feed in either liquid or gas phase with the solid catalyst at temperatures less than 500° C., preferably less than 350° C., preferably less than 300° C., and at pressure in the range from 1 to 200 atmospheres, preferably from 1 to 100 atmospheres, more preferably 5 to 50 atmospheres. The isomerization process may be carried out either in the presence or absence of hydrogen, more preferably in the presence of hydrogen. The mole ratio of hydrogen to hydrocarbon is preferably in the range of 0.01:1 to 10:1.

It may be desirable to incorporate the present catalyst with another material to improve its properties. Such materials include active and inactive materials and synthetic or naturally occurring zeolites as well as inorganic materials such as clays, silica, and/or metal oxides. The latter may be either naturally occurring or in the form of gelatinous precipitates, sols, or gels including mixtures of silica and metal oxides.

It is noted that the present catalyst need not contain any sulfate ion (U.S. Pat. No. 4,918,041). It is believed that the present catalyst is more stable and also much easier to regenerate than sulfated catalysts, such as the superacid sulfated catalysts referred to in the aforementioned article by K. Arata and M. Hino in *Proceedings 9th International Congress on Catalysis*, Volume 4, pages 1727–1735 (1988).

In the present isomerization process, n-paraffinic and monomethyl branched paraffinic components are isomerized to higher branched paraffins which are generally better octane boosters. By way of illustration, the significance of these reactions can be gleaned from a review of the following table of Octane Numbers of Pure Hydrocarbons from P. H. Emmett, ed., *Catalysis*, Vol. VI (1958).

| Octane Numbers of Pure Hydrocarbons | |
| --- | --- |
| Hydrocarbon | Blending Research Octane Number (clear) |
| Paraffins: | |
| n-heptane | 0 |
| 2-methylhexane | 41 |
| 3-methylhexane | 56 |
| 2,2-dimethylpentane | 89 |
| 2,3-dimethylpentane | 87 |
| 2,2,3-trimethylbutane | 113 |

The feedstock for the present process may be one which contains significant amounts of $C_5$+normal and/or slightly branched paraffins. In addition, the feedstock may contain monocyclic aromatic compounds and/or cyclic paraffins, such as cyclohexane. Among the hydrocarbons having 6 or less carbon atoms in the feedstock, at least 1 wt. %, e.g., at least 5 wt. %, e.g., at least 10 wt. %, e.g., at least 20 wt. %, e.g., at least 30 wt. %, of these hydrocarbons may be cyclic hydrocarbons, e.g., aromatics or cyclic paraffins.

The present catalyst may be used to isomerize $C_4$–$C_8$ paraffin hydrocarbons, either as pure compounds or mixtures. In refinery operations, the paraffins will normally be present in mixtures and, in addition to the $C_4$–$C_8$ materials, may contain hydrocarbons boiling outside this range; cycloparaffins and aromatics may also be present. Thus, the feed will comprise $C_4$–$C_8$ paraffins such as butane, pentane, hexane and these may be present in refinery streams such as raffinate cuts from solvent extraction units, reformer feedstock or pyrolysis gasoline from ethylene crackers. The feeds may also contain cyclic hydrocarbons, e.g., in the form of $C_6$+naphthas; the cyclic materials in such feeds may undergo ring opening reactions in the presence of the catalyst with its associated metal component, to form paraffins which then undergo isomerization to iso-paraffins which can be separated from the cyclics by fractionation with the cyclics being recycled to extinction. In addition to pure paraffin feeds ($C_4$–$C_8$), mixed paraffin-olefin feeds containing significant levels of olefin may be utilized.

The isomerization is carried out in the presence of the catalyst, preferably in the presence of hydrogen. Reaction temperatures are suitably in the range of about 200° to 800° F. (about 93° to 425° C.); temperatures outside this range may be utilized although they are normally less preferred; temperatures from about 300° to 700° F. (about 149° to 370° C.) are typical. Pressures will normally be up to about 1000 psig (about 7,000 kPa abs.) although there is no reason why higher pressures should not be utilized. Lower pressures, in the range of about 50 to 600 psig (about 445 to 790 kPa abs.) may readily be employed and the use of relatively low pressures within this range will generally be preferred in order to permit the use of low pressure equipment. The isomerization is usually carried out in the presence of hydrogen, typically at a molar ratio relative to the feed from 0.01 to 10:1 and usually from 0.5:1 to 2:1. Space velocities are typically from 0.1 to 10 LHSV and usually from 0.5 to 5 LHSV. When an additional acidic material (Lewis acid or Bronsted acid) is included in the catalyst, lower operational temperatures may be used, favoring the isomerization over the less desired cracking reactions.

The optional noble metal component of the present catalyst provides a hydrogenation-dehydrogenation component to the catalyst. Metals having a strong hydrogenation function are preferred, especially platinum and the other noble metals such as palladium, rhodium, iridium, rhenium, although other metals capable of acting as a hydrogenation component may also be used, for example, nickel, tungsten or other metals of Group VIII, either singly, in mixtures or in combination with other metals. The amount of the noble metal component may be in the range 0,001 to 5 wt. % of the total catalyst, e.g., from 0.1 to 2 wt. %. Base metal hydrogenation components may be added in somewhat greater amounts. The hydrogenation component can be exchanged onto the support material, impregnated into it or physically admixed with it. If the metal is to be impregnated into or exchanged onto the support, it may be done, for example, by treating the support with a platinum metal-containing ion. Suitable platinum compounds include chloroplatinic acid, platinous chloride and various compounds containing the platinum amine complex. The metal compounds may be either compounds in which the metal is present in the cation or anion of the compound; both types of compounds can be used. Platinum compounds in which the metal is in the form of a cation of cationic complex, e.g., $Pt(NH_3)_4Cl_2$ are particularly useful, as are anionic complexes such as the vanadate and metatungstate ions. Cationic forms of other metals are also useful since they may be exchanged onto the support or impregnated into it.

The catalyst may be subjected to a final calcination under conventional conditions in order to dehydrate the catalyst and to confer the required mechanical strength on the catalyst. Prior to use the catalyst may be subjected to presulfiding.

When a source of hydrogenation metal, such as $H_2PtCl_6$, is used as a source of a hydrogenation/dehydrogenation component in the present catalyst, it may be desirable to subject the present catalyst to extended reducing conditions, e.g., lasting more than 4 hours. Benefits of such extended reducing conditions are demonstrated in copending U.S. application Ser. No. 08/143,716, filed Nov. 1, 1993.

Higher isomerization activity may be provided by the inclusion of an additional material having Lewis or Bransted acid activity in the catalyst, especially when the catalyst comprises a porous binder material. For this purpose, both liquid and solid acid materials may be used. Examples of suitable additional acidic materials include aluminum trichloride, boron trifluoride and complexes of boron trifluoride, for example, with water, lower alcohols or esters. The maximum amount which may be added is set by the ability of the support material, especially the binder material, to sorb the added component and is readily determined by experiment.

The present catalyst may be used as the exclusive isomerization catalyst in single or multiple catalyst beds or it may be used in combination with other isomerization catalysts. For example, a feed may be first contacted with a catalyst bed comprising the present catalyst followed by contact with a second catalyst bed comprising a different catalyst, such as Pt on mordenite, Pt on zeolite beta or a chlorided platinum-alumina catalyst, as described in U.S. Pat. Nos. 4,783,575 and 4,834,866. The temperature of the first catalyst bed may be higher than the temperature of the second catalyst bed. When the present catalyst is called upon to cause extensive ring opening, especially in an initial catalyst bed, relatively high temperatures, e.g., as high as 500° C., and/or relatively high pressures, e.g., as high as 200 atmospheres, may be employed.

The present catalyst can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the catalyst can be extruded before drying or partially dried and then extruded. The present catalyst may be composited with a matrix material to form the finished form of the catalyst and for this purpose conventional matrix materials such as alumina, silica-alumina and silica are suitable with preference given to silica when a non-acidic binder is desired. Other binder materials may be used, for example, titania, zirconia and other metal oxides or clays. The active catalyst may be composited with the matrix in amounts from 80:20 to 20:80 by weight, e.g., from 80:20 to 50:50 active catalyst:matrix. Compositing may be done by conventional means including mulling the materials together followed by extrusion of pelletizing into the desired finished catalyst particles.

The catalyst may be treated by conventional pre-sulfiding treatments, e.g., by heating in the presence of hydrogen sulfide, to convert oxide forms of the metal components to their corresponding sulfides.

Although the use of the present catalyst in isomerization reactions has been emphasized hereinabove, it will be appreciated that this catalyst is useful for a variety of organic, e.g., hydrocarbon, compound conversion processes. When the present catalyst comprises a hydrogenation/dehydrogenation component, it may be used in reactions requiring the use of a dual-functional (1) acidic and (2) hydrogenation/dehydrogenation catalyst. Such conversion processes include, as non-limiting examples, hydrocracking hydrocarbons with reaction conditions including a temperature of from about 100° C. to about 700° C., a pressure of from about 0.1 atmosphere (bar) to about 30 atmospheres, a weight hourly space velocity of from about 0.1 to about 20, and a hydrogen/hydrocarbon mole ratio of from about 0 to about 20; dehydrogenating hydrocarbon compounds with reaction conditions including a temperature of from about 300° C. to about 700° C., a pressure of from about 0.1 atmosphere to about 10 atmospheres and a weight hourly space velocity of from about 0.1 to about 20; converting paraffins to aromatics with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting olefins to aromatics, e.g., benzene, toluene and xylenes, with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; transalkylating aromatic hydrocarbons in the presence of polyalkylaromatic hydrocarbons with reaction conditions including a temperature of from about 100° C. to about 500° C., a pressure of from about atmospheric to about 200 atmospheres, a weight hourly space velocity of from about 10 to about 1000 and an aromatic hydrocarbon/polyalkylaromatic hydrocarbon mole ratio of from about 0.3/1 to about 20/1, and a hydrogen/hydrocarbon mole ratio of from about 0 to about 20; and transferring hydrogen from paraffins to olefins with reaction conditions including a temperature from about −25° C. to about 400° C., e.g., from about 75° C. to about 200° C., a pressure from below atmospheric to about 5000 psig, e.g., from about atmospheric to about 1000 psig, a mole ratio of total paraffin to total olefin of from about 1:2 to about 500:1, e.g., from about 5:1 to about 100:1; and a weight hourly space velocity based on olefin of from about 0.01 to about 100, e.g., from about 0.05 to about 5.

The present catalyst may also be used in an isoparaffin/olefin alkylation process. The isoparaffin may be isobutane and the olefin may be propylene and/or butene(s), e.g., 2-butene. The isoparaffin/olefin alkylation reaction may take place in the presence or absence of a hydrogenation/dehydrogenation component, in the presence or absence of cofed hydrogen, at a temperature of from about −25° C. to about 400° C. with 75° being a more preferred upper limit, at a pressure from below atmospheric to about 5000 psig, at a weight hourly space velocity based on olefin of from about 0 01 to 100 hr$^{-1}$, and at a mole ratio of total isoparaffin to total olefin of from about 1:2 to about 500:1.

The present catalyst may also be used in various hydroprocessing reactions, such as the removal of metals, nitrogen and/or sulfur from feedstocks, such as resins, including such elements, particularly in the form of heteroatoms. These hydroprocessing reactions comprise contacting the feedstock along with a sufficient amount of hydrogen with the present catalyst under conditions sufficient to remove metals, nitrogen, and/or sulfur.

EXAMPLE 1

Five hundred grams of $ZrOCl_2 \cdot 8H_2O$ were dissolved with stirring in 7.5 liters of distilled water. 263 mL of conc. $NH_4OH$ were added dropwise over a 30–45 minute period to precipitate the $Zr(OH)_4$ and adjust the pH to approximately 9. The product formed was recovered by filtration and washed with excess water. The solid product was then reslurried in excess water, pH adjusted to 9 (with conc. $NH_4OH$), and refluxed overnight. This product was recovered by filtration and dried overnight at 95° C. A solution of 54 grams of $(NH_4)_6H_2W_{12}O_{40} \cdot xH_2O$ dissolved in 100 ml of $H_2O$ was then impregnated on this dried product and this resultant material was calcined in air to 825° C. for 3 hours.

EXAMPLE 2

Five hundred grams of $ZrOCl_2 \cdot 8H_2O$ were dissolved with stirring in 7.0 liters of distilled water. A solution containing 263 mL of conc. $NH_4OH$, 500 mL of distilled $H_2O$, and 54 grams of $(NH_4)_6H_2W_{12}O_{40} \cdot xH_2O$ was added dropwise over a 30–45 minute period. The pH of the solution was approximately 9. This slurry was allowed to mix at room temperature overnight. The product formed was recovered by filtration, washed with excess water, and dried overnight at 85° C. The material was then calcined in air to 825° C. for 3 hours.

EXAMPLE 3

Three hundred sixty grams of $ZrO(NO_3)_2 \cdot xH_2O$ were dissolved with stirring in 7.5 liters of distilled water. A solution containing 263 mL of conc. $NH_4OH$, 250 mL of distilled $H_2O$, and 54 grams of $(NH_4)_6H_2W_{12}O_{40} \cdot xH_2O$ was added dropwise over a 30–45 minute period. The pH of the solution was approximately 9. This slurry was then placed in the steambox overnight. The product formed was recovered by filtration, washed with excess water, and dried overnight at 85° C. The material was then calcined in air to 825° C. for 3 hours.

EXAMPLE 4

Five hundred grams of $ZrOCl_2 \cdot 8H_2O$ were dissolved with stirring in 7.0 liters of distilled water. A solution containing 263 mL of conc. $NH_4OH$, 500 mL of distilled $H_2O$, and 54 grams of $(NH_4)_6H_2W_{12}O_{40} \cdot xH_2O$ was added dropwise over a 30–45 minute period. The pH of the solution was approximately 9. This slurry was then placed in the steambox overnight. The product formed was recovered by filtration, washed with excess water, and dried overnight at 85° C. The material was then calcined in air to 825° C. for 3 hours.

EXAMPLE 5

This Example describes the activity of the catalyst of Example 1 for n-hexane conversion at 220° C., 450 psig, 1 LHSV, and 1.5 $H_2$/n-$C_6$ mole ratio. Reaction products were analyzed by on-line gas chromatography. The catalyst was pretreated prior to catalytic testing at 350° C. for one hour in flowing hydrogen, then at 500° C. for one hour in flowing nitrogen. The experimental results are shown in column 1 of Table 1.

EXAMPLE 6

This Example describes the n-hexane conversion results obtained from the catalyst of Example 2. Operating and pretreatment conditions of the catalyst are similar to those described in Example 5. The results are presented in column 2 of Table 1. The higher activity of the improved catalyst (Example 6) compared to the catalyst of Example 5 is apparent when comparing $C_4$- yield (cracking product).

EXAMPLE 7

This Example describes the n-hexane conversion results obtained from the catalyst of Example 3. Operating and pretreatment conditions of the catalyst are similar to those described in Example 5. The results are presented in column 3 of Table 1. The higher activity of the improved catalyst (Example 7) compared to the catalyst of Example 5 is apparent when comparing the $C_4$- yield (cracking product).

TABLE 1 n-Hexane Conversion Data from Examples 5–7

| | Example | | |
|---|---|---|---|
| | 5 | 6 | 7 |
| Product composition, wt. % | | | |
| $C_1 + C_2$ | 0.02 | 0.02 | — |
| $C_3$ | 1.0 | 2.4 | 2.5 |
| $i-C_4$ | 4.3 | 12.4 | 9.9 |
| $n-C_4$ | 0.6 | 1.2 | 1.0 |
| $i-C_5$ | 6.0 | 6.8 | 5.7 |
| $n-C_5$ | 1.3 | 1.3 | 0.9 |
| 2,2-dimethyl butane | 7.2 | 5.4 | 5.8 |
| 2,3-dimethyl butane | 8.4 | 7.6 | 7.2 |
| 2-methyl pentane | 29.0 | 25.7 | 26.7 |
| 3-methyl pentane | 18.3 | 15.8 | 16.9 |
| n-hexane | 21.1 | 20.2 | 19.8 |
| $C_7+$ | 2.8 | 1.1 | 3.1 |
| $C_4-$ yield, wt. % | 5.9 | 16.0 | 13.3 |

EXAMPLE 8

Normal pentane conversion was carried out over catalyst from Example 1 at 232° C., 350 psig, 2 LHSV, and 2 $H_2/n-C_5$ mol ratio. The catalyst was calcined at 300° C. in flowing nitrogen for one hour prior to catalytic testing. The results are shown in column 1 of Table 2.

EXAMPLE 9

This Example describes the activity for n-pentane conversion for catalyst of Example 4. Operating and catalyst pretreatment conditions were similar to those described in Example 8. The experimental results are shown in column 2 of Table 2. The higher activity of Example 9 (improved catalyst) compared to Example 8 is apparent when comparing the $C_4$-yield (cracking product).

TABLE 2 n-Pentane Conversion Data from Examples 8–9

| | Example | |
|---|---|---|
| | 8 | 9 |
| Product composition, wt. % | | |
| $C_1 + C_2$ | 1.0 | 0.8 |
| $C_3$ | 1.2 | 2.5 |
| $i-C_4$ | 6.1 | 20.2 |
| $n-C_4$ | 0.5 | 1.2 |
| $i-C_5$ | 66.5 | 51.3 |
| $n-C_5$ | 23.2 | 21.0 |
| $C_6+$ | 1.4 | 2.9 |
| $C_4-$ yield, wt. % | 8.8 | 24.7 |

The present catalysts, especially tungstate-modified zirconia catalysts, are useful in a number of hydrocarbon conversion processes, particularly those which are catalyzed by strongly-acidic acid catalysts. The present method involves the co-precipitation of the catalyst components.

This new method significantly reduces the complexity of the synthesis, addresses potential environmental concerns of manufacturing, and provides avenues for enhancing the activity and flexibility of this acid catalyst system. The co-precipitation method can be further modified by changing the synthesis pH, reaction temperature, and solvent to alter the physical characteristics of this catalyst (i.e., pore size distribution, surface area, etc.). Furthermore, the co-precipitation can also include other additives (metals) or co-catalysts that will change the activity and selectivity of the hydrocarbon conversion products. For example, platinum could be co-precipitated with the tungsten to produce an active catalyst for the isomerization of light paraffins, thus eliminating a secondary platinum impregnation step. Another example would be the addition of a high surface area oxide such as silica (e.g., M41S support) to enhance the final surface area of the zirconia-based catalyst.

What is claimed is:

1. A method for preparing a catalyst comprising an acidic solid comprising a Group IVB metal oxide modified with an oxyanion of tungsten, said method comprising co-precipitating the Group IVB metal oxide along with the oxyanion of tungsten, followed by calcining the co-precipitate at a temperature from about 750° C. to about 900° C.

2. A method according to claim 1, wherein the source of said oxyanion of tungsten is $(NH_4)_2WO_4$ or $WCl_6$.

3. A method according to claim 1, wherein the source of said oxyanion of tungsten is selected from the group consisting of ammonium metatungstate, tungsten chloride, tungsten carbonyl, tungstic acid, and sodium tungstate.

4. A method according to claim 1, wherein said Group IVB metal is Zr.

5. A method for preparing a catalyst comprising an acidic solid comprising tungstate modified zirconia, said method comprising the steps of:

(a) combining a first liquid solution with a second liquid solution, said first solution comprising a source of zirconia dissolved in water and said second solution comprising a source of tungstate dissolved in water;

(b) maintaining the combined solutions of step (a) under conditions sufficient to form a solid co-precipitate comprising tungstate-modified zirconia;

(c) recovering the solid co-precipitate from step (b) by filtration; and (d) calcining the recovered co-precipitate from step (c) at a temperature from about 750° C. to about 900° C.

6. A method according to claim 5, wherein said source of zirconia is $ZrOCl_2$.

7. A method according to claim 6, wherein said source of tungstate is ammonium metatungstate.

8. A method according to claim 7, wherein the combined solutions of step (b) are maintained at a pH of 9.

9. A method according to claim 8, wherein said second liquid solution further comprises ammonium hydroxide.

10. A method according to claim 9, wherein step (a) comprises the dropwise addition of said second liquid solution to said first liquid solution.

11. A method according to claim 10, wherein calcination step (d) comprises heating the recovered co-precipitate in an oxidizing atmosphere.

12. A method according to claim 11, wherein calcination step (d) comprises heating the recovered co-precipitate in air at a temperature from about 750° C. to about 850° C. for a calcination time of about 0.1 to 10 hours.

13. A method according to claim 5, wherein said combined solutions in step (b) are maintained at a temperature of less than 200° C.

14. A method according to claim 13, wherein said combined solutions in step (b) are maintained at a temperature of at least ambient temperature.

15. A method according to claim 5, wherein said combined solutions in step (b) are maintained at a temperature of from about 50° C. to about 100° C.

16. A method according to claim 5, wherein said catalyst has a calculated mole ratio, expressed in the form of $ZrO_2/WO_3$, of from 2 to 100.

17. A method according to claim 5, wherein said catalyst has a calculated mole ratio, expressed in the form of $ZrO_2/WO_3$, of from 4 to 30.

* * * * *